United States Patent [19]
Williams et al.

[11] Patent Number: 4,853,372
[45] Date of Patent: Aug. 1, 1989

[54] NON-AQUEOUS IVERMECTIN FORMULATION WITH IMPROVED ANTIPARASITIC ACTIVITY

[75] Inventors: James B. Williams, Freehold; Russell U. Nesbitt, Somerville, both of N.J.

[73] Assignee: Merck & Co., Inc., Rahway, N.J.

[21] Appl. No.: 935,914

[22] Filed: Nov. 28, 1986

Related U.S. Application Data

[63] Continuation of Ser. No. 767,463, Aug. 20, 1985, abandoned, which is a continuation of Ser. No. 564,140, Dec. 22, 1983, abandoned.

[51] Int. Cl.$^4$ .......................................... A61K 31/71
[52] U.S. Cl. ...................................... 514/30; 514/970
[58] Field of Search ................................ 514/30, 970; 424/DIG. 10, 405

[56] References Cited

U.S. PATENT DOCUMENTS

| | | | |
|---|---|---|---|
| 3,915,955 | 10/1975 | Cooper et al. | 260/210 AB |
| 4,199,569 | 4/1980 | Chabala et al. | 514/30 |
| 4,201,861 | 5/1980 | Mrozik et al. | 536/17 A |
| 4,389,397 | 6/1983 | Lo et al. | 514/53 |

Primary Examiner—Johnnie R. Brown
Assistant Examiner—Jacqueline M. Stone
Attorney, Agent, or Firm—David L. Rose; Michael C. Sudol

[57] ABSTRACT

Ivermectin, an antiparasitic agent which is insoluble and unstable in water, is formulated in glycerol formal and propylene glycol. These liquid formulations are suitable for parenteral administration for the treatment of parasitic infections and demonstrate improved efficacy and a broadened spectrum over previous formulations.

1 Claim, No Drawings

NON-AQUEOUS IVERMECTIN FORMULATION WITH IMPROVED ANTIPARASITIC ACTIVITY

This is a continuation, of application Ser. No. 767,463, filed Aug. 20, 1985, which in turn is a continuation of Ser. No. 564,140, filed Dec. 22, 1983, both now abandoned.

BACKGROUND OF THE INVENTION

Ivermectin and the avermectin family, of which ivermectin is a member, is a series of new and very potent antiparasitic agents which are useful against a broad spectrum of endoparasites and ectoparasites in mammals as well as having agricultural uses against various parasites found in and on crops and in soil. Ivermectin is disclosed in U.S. Pat. No. 4,199,569, issued Apr. 22, 1980 to Chabala and Fisher. Ivermectin is a mixture, in the ratio of approximately 80:20 of 22,23-dihydro C-076 B1a and B1b. In administering ivermectin to animals it is very convenient to use parenteral formulations to administer the drug. While an aqueous micelle formulation (see U.S. Pat. No. 4,389,397) is useful for parenteral administration, higher activity has been observed against endoparasites than ectoparasites. It is known that ivermectin can be useful against ectoparasites and it is desireable to have a parenteral formulation with high levels of both endo-and ectoparasiticidal activity.

Thus, it is desirable to prepare a parenteral liquid formulation of ivermectin which has activity against internal and external parasites. Ivermectin has very poor solubility in water, at a level of about 0.005 mg per ml at room temperature, but is very soluble in many organic solvents.

It was unexpectedly discovered during the investigation of the instant organic parenteral formulations that both endo- and ectoparasiticidal activity was observed which was not observed with the aqueous micelle formulation.

Ivermectin is a member of a family of compounds identified as avermectins. The basic avermectin compounds are isolated from the fermentation broth of the microorganism *Streptomyces avermitilis*. Such compounds are described in U.S. Pat. No. 4,310,519. In addition, certain derivatives of these basic fermentation products have been prepared.

Some of the avermectins contain a 22,23-double bond. This may be selectively reduced to prepare the ivermectin compounds discussed above. In addition, the avermectins possess a disaccharide moiety at the 13-position consisting of the a-L-oleandrosyl-a-L-oleandrosyl group. One or both of these saccharide groups may be removed as described in U.S. Pat. No. 4,206,205. The thus produced aglycone derivatives have a hydroxy group at the 13-position. This group may be removed to form the 13-deoxy compound as described in U.S. Pats. Nos. 4,171,314 and 4,173,571. On the avermectin compounds and derivatives are several hydroxy groups which may be acylated as described in U.S. Pat. No. 4,201,861.

It is anticipated that the process and formulation of the instant invention can be carried out on the foregoing compounds since all such compounds share to an only slightly varying degree, the spectrum of biological activity of the ivermectin compound.

In addition, a series of compounds identified as milbemycin compounds have the same 16 membered macrocyclic ring as do the avermectin compounds, although they do not have the disaccharide moiety and also differ in the nature of other substituent groups. These compounds are disclosed in U.S. Pat. No. 3,950,360 and they also would be expected to benefit in their spectrum of activity by the instant process and formulations.

SUMMARY OF THE INVENTION

The instant invention concerns the preparation of an avermectin parenteral formulation generally and in particular ivermectin, a new anthelmintic agent, using glycerol formal and propylene glycol. A variation of this formulation replaces the glycerol formal with water at a lower concentration to achieve the same expanded profile of activity. Thus, it is an object of this invention to describe such a formulation. A further object is to describe the solvents used to prepare such parenteral formulations. A still further object is to describe the enhanced biological profile which is achieved with these new formulations. Further objects will become apparent from a reading of the following description.

DESCRIPTION OF THE INVENTION

The instant invention resides in the unexpected expansion of the spectrum of activity of avermectin compounds which is achieved with the use of the below described parenteral formulation. The instant parenteral formulation consist of an avermectin compound, glycerol formal and propylene glycol. The avermectin compound is present in the formulation at a level of from 0.1 to 20% by weight, preferably about 1% by weight. The avermectin compound is dissolved in a solvent mixture of glycerol formal and propylene glycol which are in a ratio of from 10:90 to 90:10 in ratios of volume to volume (V/V). It is preferred to use a ratio of about 40:60 V/V.

A variation of this formulation replaces the glycerol formal with water. The formulation uses ratios of propylene glycol to water of from 95:5 to 80:20 V/V preferably about 90:10 V/V.

To prepare the instant formulations the avermectin compound is dissolved in either the glycerol formal or propylene glycol and, when dissolution is complete, the remaining solvents are added to prepare the final concentration of drug and ratio of solvents.

Since the formulation is for parenteral uses it must be sterilized, thus the final step is sterilization by non-heating means since the active ingredient might be subject to decomposition at autoclave temperatures. Membrane filtration is the preferred means of sterilization.

The unexpected feature of this invention is realized in its comparison with other injectable formulations containing avermectin compounds. The aqueous micelle formulation provides dosages of avermectin compounds which are sufficient to eradicate substantially all internal parasites of the host animal. It was desired to obtain a parenteral formulation which also had high levels of activity against both internal and external parasites.

The instant formulation achieves the desired result as demonstrated in the following test:

A comparison of the efficacy of ivermectin when administered to cattle by means of the instant formulation or by an aqueous micelle formulation shows the superiority of the instant formulation, particularly towards ectoparasites.

Cattle that had been infected with ticks (*Boophilus microplus*) were given a control placebo or equal doses of ivermectin via the formulation of Example 1, or an aqueous micelle formulation. The efficacy of the treatment was measured by counting the ticks in the manner described by Wharton et. al. in *Australian Journal of Agricultural Research* 21 pages 985–1006 (1970). The prolonged effects of the drug were observed by counting the ticks several times over a 4-week period with a constant natural exposure to tick infestation.

The test showed that, to a statistically significant degree, both formulations had fewer ticks than the controls. At the end of the trial there were statistically significantly more ticks on the micelle treated cattle than on the cattle treated with the instant formulation thus demonstrating greater efficacy and duration of efficacy for the instant formulation.

The following examples are provided in order that the invention might be more fully understood. They should not be considered as being limitations of the invention.

EXAMPLE 1

To prepare an ivermectin injectable solution containing 10 mg of active ingredient per ml of solution the following ingredients were used:
Ivermectin: 1.0% W/V
Glycerol Formal: 40.0% V/V
Propylene Glycol: q.s. 100.0% V/V The ivermectin was dissolved in either the glycerol formal, the propylene glycol or a mixture of the solvents. When the dissolution was complete the volume was adjusted to the final desired volume. The final solution was sterilized by membrane filtration and packaged aseptically providing 10 mg of ivermectin per ml of solution.

EXAMPLE 2

To prepare an ivermectin injectable solution containing 10 mg of active ingredient per ml of solution, the following ingredients were used:
Ivermectin: 1.0% W/V
Water for Injection: 10.0% V/V
Propylene Glycol: q.s. 100.0% V/V The ivermectin was dissolved in a part of the propylene glycol. The water for injection was added such that precipitation of the ivermectin was avoided and the final volume was adjusted with propylene glycol to the desired final concentration. The solution was membrane filtered to sterilize it and packaged aseptically.

What is claimed is:

1. An endo or ectoparasiticidal parenteral formulation consisting of from 0.1 to 20% by weight of ivermectin dissolved in a combination of propylene glycol and glycerol formal in a ratio of about 60:40 v/v.

* * * * *